US006455053B1

(12) United States Patent
Okada et al.

(10) Patent No.: US 6,455,053 B1
(45) Date of Patent: Sep. 24, 2002

(54) QUICKLY SOLUBLE SOLID PREPARATIONS

(75) Inventors: Minoru Okada, Inzai; Yasuo Ikeda, Narashino; Kenji Ono, Sakura; Toshiaki Kurazumi; Syuichi Kasai, both of Narita; Katsumi Imamori, Yotsukaido, all of (JP)

(73) Assignee: SSP Co., Ltd., Tokyo (JP)

( * ) Notice: Subject to any disclaimer, the term of this patent is extended or adjusted under 35 U.S.C. 154(b) by 0 days.

(21) Appl. No.: 09/509,988

(22) PCT Filed: Oct. 7, 1998

(86) PCT No.: PCT/JP98/04526

§ 371 (c)(1),
(2), (4) Date: May 24, 2000

(87) PCT Pub. No.: WO99/18936

PCT Pub. Date: Apr. 22, 1999

(30) Foreign Application Priority Data

Oct. 9, 1997 (JP) .............................. 9-291841
Oct. 9, 1997 (JP) .............................. 9-291842
Oct. 9, 1997 (JP) .............................. 9-291843

(51) Int. Cl.[7] .......................... A61K 9/00; A61K 9/20; A61K 9/14
(52) U.S. Cl. .................. 424/400; 424/464; 424/465; 424/484; 424/488
(58) Field of Search ................. 424/494, 435, 424/400, 470, 480, 497, 486, 441, 484, 464, 465

(56) References Cited

U.S. PATENT DOCUMENTS

| 4,327,080 | A |   | 4/1982 | Wong et al. .................. 424/80 |
| 4,882,144 | A |   | 11/1989 | Hegasy ........................ 424/80 |
| 5,039,540 | A |   | 8/1991 | Ecanow ...................... 426/385 |
| 5,079,018 | A |   | 1/1992 | Ecanow ...................... 426/385 |
| 5,244,881 | A |   | 9/1993 | Coutel-Egros ............... 514/58 |
| 5,320,848 | A | * | 6/1994 | Geyer et al. ................ 424/441 |
| 5,328,903 | A |   | 7/1994 | Ishii et al. .................. 514/168 |
| 5,464,632 | A |   | 11/1995 | Cousin et al. ............... 424/465 |
| 5,466,464 | A |   | 11/1995 | Masaki et al. ............... 424/434 |
| 5,576,014 | A | * | 11/1996 | Mizumoto et al. .......... 424/435 |
| 5,876,759 | A | * | 3/1999 | Gowan, Jr. .................. 424/494 |
| 5,980,941 | A | * | 11/1999 | Raiden et al. ............... 424/464 |

FOREIGN PATENT DOCUMENTS

| JP | 53-44619 | 4/1978 |
| JP | 58-10513 | 1/1983 |
| JP | 58-83617 | 5/1983 |
| JP | 58-113124 | 7/1983 |
| JP | 58-194808 | 11/1983 |
| JP | 2-32014 | 2/1990 |
| JP | 4-13625 | 1/1992 |
| JP | 3-56412 | 9/1993 |
| JP | 5-271054 | 10/1993 |
| JP | 5-310558 | 11/1993 |
| JP | 6-502194 | 3/1994 |
| JP | 6-183964 | 7/1994 |
| JP | 8-99904 | 4/1996 |
| JP | 8-143473 | 6/1996 |
| JP | 8-208520 | 8/1996 |
| JP | 8-208521 | 8/1996 |
| JP | 8-333243 | 12/1996 |
| JP | 9-48726 | 2/1997 |
| JP | 9-71523 | 3/1997 |
| WO | WO 93/12769 | 7/1993 |
| WO | WO 95/01782 | 1/1995 |

* cited by examiner

*Primary Examiner*—Thurman K. Page
*Assistant Examiner*—Blessing Fubara
(74) *Attorney, Agent, or Firm*—Crowell & Moring LLP

(57) ABSTRACT

An orally administrable uncompressed rapidly dissolving molded dosage form comprises a drug and either one or more saccharides or one saccharide and polyvinylpyrrolidone. Saccharides are chosen and used in proportion based on their solubilities. Methods for producing uncompressed rapidly dissolving solid preparations comprise mixing a drug and carriers according to the present invention and charging the mixture in a mold. Rapidly dissolving oral dosage forms facilitate administration of drugs to patients having a difficulty in swallowing such as children and the elderly.

20 Claims, No Drawings

QUICKLY SOLUBLE SOLID PREPARATIONS

TECHNICAL FIELD

The present invention relates to a rapidly dissolving solid preparation. More particularly, it relates to a rapidly dissolving solid preparation which rapidly disintegrates and dissolves at the ingestion site where there occurs a limited amount of moisture such as the interior of the oral cavity.

BACKGROUND ART

There has been conventionally pursued a development of a solid preparation which will rapidly disintegrate and dissolve in the oral cavity as a preparation which is easy for the patients having a difficulty in swallowing, the elderly persons, or children to ingest. For example, in each of Japanese Laid-Open Patent Publication Nos. Sho 53-44619, Sho 58-113124, Hei 3-56412 and Hei 3-86837, and Japanese National Phase PCT Laid-Open Publication No. Hei 9-502622, there is proposed a solid preparation using a lyophilization technology. Further, in Japanese Laid-Open Patent Publication No. Hei 2-32014 or Hei 5-271054, there is proposed a solid preparation based on a triturated tablet obtained by pressure-molding a wetted preparation powder under a low pressure, and subsequently drying it.

Still further, in each of Japanese Laid-Open Patent Publication No. Sho 58-194808, Japanese National Phase PCT Laid-Open Publication No. Hei 6-502194, Japanese Laid-Open Patent Publication Nos. Hei 5-310558, Hei 8-99904, Hei 8-208520, Hei 8-208521, Hei 8-333243, and Hei 9-71523, there is disclosed a solid preparation resulting from compression-molding which dissolves and disintegrates in the oral cavity. Also, in WO93/12769, there is proposed a solid preparation obtained by dispersing a mixed powder of a drug, and lactose and/or mannitol in an agar aqueous solution, filling it in a mold, and subsequently drying it.

However, each of the conventional preparations proposed above is not pharmaceutically sufficient, and includes various problems. For example, with the pressure molding method, it is possible to enhance the hardness not only by the manufacturing method based on ordinary compression molding, but also by the method based on the triturated tablet. However, the preparation obtained by this method often exhibits a longer dissolution and disintegration time in the oral cavity. Further, it sometimes requires addition of a water-insoluble disintegrator, often resulting in an unpleasant ingestion feeling when the preparation is dissolved in the oral cavity. Also, because gelatin and agar are natural substances, the solid preparation using them is susceptible to discoloration with time, may sometimes impair the stability of the drug to be combined with, and further miscellaneous germs tend to proliferate therein.

In contrast, the preparation prepared by the use of the lyophilization technique has a large void, and hence the dissolution rate in the oral cavity is very high. However, the preparation itself is bulky, and it is generally difficult to increase the drug content. Further, since it is often difficult to store and handle the preparation on a daily basis, the preparation is brittle and easy to collapse due to a low hardness, and it also has a high hygroscopicity. Especially, under the climatic conditions of high temperature and high humidity, the preparation may change its shape very easily due to moisture absorption, and only picking it up for ingestion may cause it to adhere to the finger, and these may interfere with the handling of the preparation.

DISCLOSURE OF THE INVENTION

It is an object of the present invention to provide a rapidly dissolving solid preparation which disintegrates and dissolves rapidly in the oral cavity and the like, and has a practical hardness, whereby solving foregoing problems, and a manufacturing method thereof.

In order to attain such an object, a first embodiment of the present invention provides a rapidly dissolving solid preparation obtained by mixing a drug, and a saccharide having a solubility of 30 g or less in 100 g of water at room temperature and a saccharide having a solubility of 30 g or more in 100 g of water at room temperature in water in such an amount as not to completely dissolve the saccharide having a solubility of 30 g or less in 100 g of water at room temperature, and then removing the moisture therefrom.

Further, a second embodiment of the present invention provides a rapidly dissolving solid preparation obtained by dissolving and dispersing a drug, a saccharide, and polyvinylpyrrolidone in an organic solvent, and then removing the organic solvent therefrom.

Still further, a third embodiment provides a rapidly dissolving solid preparation obtained by dissolving and/or dispersing a drug in an aqueous solution of a saccharide, and lyophilizing it.

BEST MODE FOR CARRYING OUT THE INVENTION

A rapidly dissolving solid preparation in a first embodiment to a third embodiment of the present invention is characterized by the procedure in which, a drug as well as a saccharide are dissolved and dispersed in an aqueous solution, an organic solvent, or the like, resulting in a suspension composition, and the resultant is dried to obtain the rapidly dissolving solid preparation.

Below, a detailed description will be given individually to the rapidly dissolving solid preparation in the first embodiment to the third embodiment.

The first embodiment of the rapidly dissolving solid preparation provided by the present invention is the rapidly dissolving solid preparation obtained by mixing a drug, and a saccharide having a solubility of 30 g or less in 100 g of water at room temperature and a saccharide having a solubility of 30 g or more in 100 g of water at room temperature in water in such an amount as not to completely dissolve the saccharide having a solubility of 30 g or less in 100 g of water at room temperature, and then removing the moisture therefrom.

The rapidly dissolving solid preparation of the present invention is specifically manufactured in the following manner. A drug, and a saccharide having a solubility of 30 g or less in 100 g of water at room temperature and a saccharide having a solubility of 30 g or more in 100 g of water at room temperature are mixed in water in such an amount as not to completely dissolve the saccharide having a solubility of 30 g or less in 100 g of water at room temperature to obtain a creamy suspension. Subsequently, the suspension is charged in a mold for a preparation, and then the moisture is removed therefrom.

Namely, the first rapidly dissolving solid preparation prepared by the present invention is characterized that a saccharide having both a low solubility and a high solubility in water is used in combination with a drug to produce a creamy composition which is an aqueous suspension, and the moisture is subsequently removed therefrom.

According to the study by the present inventors, if a drug and a saccharide having a low solubility in water alone are combined, the resulting suspension is not a desired creamy composition, and the separation of the drug and the saccharide from the moisture occurs during charge, making it impossible to achieve uniform charging. Further, in the solid preparation after drying the composition, irregularities will occur on the surface thereof, and hence the utility as a practical preparation is poor.

On the other hand, the composition obtained by combining a drug and a saccharide having a high solubility in water alone becomes a composition in the aqueous solution state. Therefore, drying for achieving a solid preparation cannot be carried out sufficiently with room temperature blast or suction drying, or even if drying can be performed, much time is required, resulting in poor productivity.

However, surprisingly, they have found that the solid preparation obtained by using a drug and both of the saccharide having a low solubility in water and the saccharide having a high solubility in water in combination to prepare a creamy composition which is an aqueous suspension, and subjecting the composition to air-drying or suction drying at ordinary temperature to remove the moisture therefrom is as follows. That is, the solid preparation has a practically acceptable hardness, and rapidly disintegrates and dissolves in the oral cavity and the like even without being ingested together with water. Further, complicated manufacturing process is not required, and the drug content can be increased, if required.

The saccharide having a low solubility in water to be used for the rapidly dissolving solid preparation in this embodiment of the present invention is the one which dissolves in a large quantity of water, but not in a small quantity of water, i.e., a saccharide having a solubility of 30 g or less in 100 g of water at room temperature. The type of saccharide is not particularly limited so long as it has such a solubility, and lactose, mannitol, and the like may be specifically mentioned. These can be used alone, or in combination of two or more thereof.

Further, the saccharide having a high solubility in water is a saccharide having a solubility of 30 g or more in 100 g of water at room temperature. The type of saccharide is not particularly limited so long as the saccharide has such a solubility. Specific examples of such a saccharide include fructose, glucose, sucrose, xylose, trehalose, xylitol, sorbitol, erythritol, dextrin, and pullulan. These saccharides can be used alone, or in combination of two or more thereof. They may be used in the powder form, or may be further dissolved in water to be in an aqueous solution state, and then added to a mixed powder of a drug and a saccharide having a low solubility in water.

The study by the present inventors proves as follows: it is preferred that a mixing ratio of the aforementioned saccharide having a low solubility in water to the saccharide having a high solubility in water to be added and used together with a drug in the present invention falls within the range of 98:2 to 80:20 on a solid content weight basis in order to maintain the rapid disintegration and dissolution characteristics, and perform drying in a relatively shorter time at the time of manufacturing.

Further, the total amount of the saccharide having a low solubility in water and the saccharide having a high solubility in water to be mixed into the preparation, to be used with the drug in the present invention, varies with the properties of the drug to be used and additives to be mixed therewith. However, it has been found that, in general, both the saccharides are preferably added in a total amount of 40% by weight or more, and more preferably 60% by weight or more on a total solid content basis of the solid preparation in order to maintain the practically acceptable hardness and the rapid dissolvability.

On the other hand, the content of the drug contained in the solid preparation of the present invention depends upon the dosage for one ingestion and the physico-chemical properties of the drug, but it is preferably 60% by weight or less based on the total solid content, and more preferably 40% by weight or less based on the total solid content.

Thus, the preferred embodiment of the rapidly dissolving solid preparation in the first embodiment provided by the present invention is the rapidly dissolving solid preparation obtained in the following manner. A drug in an amount of 60% by weight or less, and preferably 40% by weight or less based on the total solid content, and a saccharide having a solubility of 30 g or less in 100 g of water at room temperature and a saccharide having a solubility of 30 g or more in 100 g of water at room temperature in a solid content weight ratio of 98:2 to 80:20, and in an amount of 40% by weight or more, and preferably 60% by weight or more based on the total solid content are used to be mixed with water in such an amount so as not to completely dissolve the saccharide having a solubility of 30 g or less in 100 g of water at room temperature. Subsequently, the moisture is removed therefrom.

The rapidly dissolving solid preparation in the first embodiment of the present invention is not particularly limited in size and shape as the preparation form. For example, it can be formed in a granule, pellet, tablet, suppository, or the like, as the ordinary preparation form, and it is especially preferable to be formed in a tablet.

Such a rapidly dissolving solid preparation can be specifically manufactured by the following method. That is, to a mixed powder obtained by mixing a drug, a saccharide having a low solubility in water, and a saccharide having a high solubility in water, is added purified water to prepare a creamy suspension. Subsequently, the suspension is charged into a hole of a desired preparation mold, for example, a concave mold, and dried. Thus, an objective solid preparation can be obtained.

Mixing of the drug and the saccharide having a high solubility in water may be accomplished in such a manner that one is dissolved in purified water to be added to the other.

Further, drying for removing the moisture from the suspension can be carried out by air-drying or suction drying at ordinary temperature.

The rapidly dissolving solid preparation of the present invention having the first embodiment manufactured as aforementioned method rapidly disintegrates and dissolves in the oral cavity without specifically adopting the processes such as pressure molding and freeze-drying.

On the other hand, the present invention provides the rapidly dissolving solid preparation as one embodiment of the second embodiment wherein, a drug, a saccharide, and polyvinylpyrrolidone are dissolved and dispersed in an organic solvent, and subsequently the organic solvent was removed therefrom.

Such a rapidly dissolving solid preparation is specifically manufactured in the following manner. A drug, a saccharide, and polyvinylpyrrolidone are dissolved and dispersed in an organic solvent to obtain a suspension. Subsequently, the suspension is charged into a mold for a preparation, and then the organic solvent is removed therefrom.

That is, the rapidly dissolving solid preparation in the second embodiment of the present invention is characterized by the procedure, wherein, a saccharide and polyvinylpyrrolidone are used in combination with a drug to be dissolved and dispersed in an organic solvent, resulting in a suspension, and then the organic solvent is removed therefrom.

The saccharide to be used in such a rapidly dissolving solid preparation in the second embodiment is not particularly limited so long as it is dissolvable in water. Examples of the saccharide which can be used include monosaccharide, disaccharide, oligosaccharide, sugar alcohol, reducing sugar, and isomerized sugar. More specific examples thereof include glucose, fructose, lactose, maltose, sucrose, xylose, trehalose, dextrin, sorbitol, xylitol, mannitol, erythritol, maltitol, lactitol, and lactulose. These types can be used alone, or in mixture of two or more thereof.

In the rapidly dissolving solid preparation of the present invention, the amount of the aforesaid saccharide, to be used with a drug, to be added into the preparation varies depending upon the properties of the drug used, and the additive to be used together. In order to maintain the practical hardness and the rapid dissolvability, in general, it is added preferably in an amount of 40% by weight or more, and more preferably in an amount of 60% by weight or more in terms of the total solid content of the preparation.

Also, the amount of polyvinylpyrrolidone to be used with the drug and the saccharide varies depending upon the properties of the drug and the additives to be mixed with. However, in order to maintain the practical hardness and the rapid dissolvability, in general, it is added preferably in an amount of 1 to 20% by weight, and more preferably in an amount of 2 to 15% by weight in terms of the total solid content of the preparation.

Further, in the rapidly dissolving solid preparation in the second embodiment of the present invention, the organic solvent for dissolving and dispersing the drug, the saccharide, and polyvinylpyrrolidone is not particularly limited so long as it well dissolves polyvinylpyrrolidone, but the saccharide is dissolved not as well. Particularly preferred specific examples thereof include ethanol. Also, such an organic solvent in the present invention can be used in the form of a mixed solution with water. When it is used in the form of the mixed solution, the water is preferably in an amount of 30% by weight or less based on the total amount of the solvent.

On the other hand, the amount of the drug contained in the solid preparation of the present invention depends upon the dosage for one ingestion and the physico-chemical properties of the drug, but it is preferably 60% by weight or less based on the total solid content, and more preferably 40% by weight or less based on the total solid content.

Thus, the present invention presents as the preferred embodiment of the rapidly dissolving solid preparation in the second embodiment, wherein, a drug in an amount of 60% by weight or less, and preferably 40% by weight or less based on the total solid content, and a saccharide in an amount of 40% by weight or more, and preferably 60% by weight or more based on the total solid content, and polyvinylpyrrolidone in an amount of 1 to 20% by weight, and preferably of 2 to 15% by weight are dissolved and dispersed in an organic solvent which is ethanol or a mixed solution of ethanol and water, followed by drying.

For the rapidly dissolving solid preparation in the second embodiment of the present invention, the size and shape thereof as the preparation form are also not particularly limited. For example, the preparation can be formed in a granule, pellet, tablet, suppository, or the like, as the ordinary preparation form, and , a tablet form is especially preferred.

Such a rapidly dissolving solid preparation can be specifically manufactured by the following method. That is, to a mixed powder of a drug, a saccharide, and polyvinylpyrrolidone, is added an organic solvent to dissolve and disperse it, resulting in a suspension. Subsequently, the resultant is charged into a hole of a desired preparation mold, for example, a concave mold, and dried, to obtain an objective solid preparation.

Further, polyvinylpyrrolidone may be dissolved in an organic solvent, and then added to the mixed powder of a drug and a saccharide. Still further, drying can be carried out by air-drying or suction drying at normal temperature.

The rapidly dissolving solid preparation of the present invention in the second embodiment produced by aforementioned method is made to be a solid preparation which rapidly disintegrates and dissolves in the oral cavity without the processes such as pressure molding and lyophilization.

The present invention presents the rapidly dissolving solid preparation as one embodiment of the third embodiment provided, wherein, a drug is dissolved and/or dispersed in an aqueous solution of a saccharide, and lyophilized.

Namely, the present inventors has conducted a study on a solid preparation which rapidly dissolves in the environment where only the limited amount of moisture is present such as the interior of the oral cavity, obtained by the lyophilizing method, in addition to the rapidly dissolving solid preparations in the foregoing first and second embodiments. As a result, they have found the following fact. That is, freeze-drying can be accomplished in a relatively short period of time by using a specific kind of aqueous solution of a saccharide such as lactose, trehalose, mannitol, sorbitol, erythritol, or dextrin as an excipient out of the aqueous solutions of various excipients capable of dissolving or dispersing the drug, and dispersing and/or dissolving the drug in the aqueous solution and then lyophilizing it. When the concentration of the aqueous solution of the saccharide for dispersing and/or dissolving the drug falls within a range of 10 to 30% by weight, a practical hardness can be imparted to the lyophilized solid preparation, and the rapid dissolvability in the oral cavity can be obtained.

Thus, the present invention presents the rapidly dissolving solid preparation as the preferred embodiment of the third embodiment, wherein, a drug is dissolved and/or dispersed in a 10–30 wt % aqueous solution of one or more than one saccharides selected from lactose, trehalose, mannitol, sorbitol, erythritol, and dextrin, and lyophilized. As the particularly preferred embodiment, there is provided the rapidly dissolving solid preparation wherein the aqueous solution of the saccharide for dissolving and/or dispersing the drug is an aqueous solution of trehalose and/or dextrin.

Such a rapidly dissolving solid preparation is specifically produced by dissolving and/or dispersing the drug in the aqueous solution of the saccharide to form a suspension composition, subsequently, charging the resultant in a mold for a preparation, and then lyophilizing.

Namely, the third embodiment of the rapidly dissolving solid preparation provided by the present invention is characterized in that the drug is dissolved and/or dispersed in an aqueous solution of a specific type of saccharide, having a specific concentration, and then lyophilized.

Examples of the preferred saccharide to be used in such a rapidly dissolving solid preparation in the third embodiment include lactose, trehalose, mannitol, sorbitol, erythritol, and dextrin. These may be used alone, or in mixture of two or more thereof. Out of these, particularly preferred are trehalose and/or dextrin. When trehalose and/or dextrin is used as a saccharide in the present invention, a solid preparation having a practical hardness can be obtained even if it is formed, for example, in a large tablet with a diameter of about 20 mm. Therefore, it can also conform to the drug which dosage per day is high. The amount of the drug contained in the solid preparation of the present invention varies depending upon the dosage for one ingestion and the physico-chemical properties of the drug, and is not particularly limited.

Further, it is found that the less the content of the aqueous solution of the saccharide is, the more the hardness of the lyophilized solid preparation is reduced. On the other hand, the higher the content of the saccharide is, the higher the hardness, longer the time for lyophilization and the dissolution time of the solid preparation becomes. Therefore, in the present invention, these saccharides may properly be used by being dissolved in water so as to be in a preferred amount of 10 to 30% by weight, and more preferably, amount of 15 to 25% by weight.

In the rapidly dissolving solid preparation in the third embodiment of the present invention, when the drug is not completely dissolved, or dispersed in the aqueous solution of the saccharide, the dispersant further described below is preferably added thereto. The dispersant is not particularly limited so long as it can disperse the drug until the suspension is lyophilized after preparing the suspension.

Examples of the particularly preferred dispersant include α-starch, partly pregelatinized starch, carboxymethyl starch sodium, methyl cellulose, hydroxypropylmethyl cellulose, hydroxypropyl cellulose, carboxymethyl cellulose sodium, powdered acacia, tragant gum, karaya gum, gaty gum, pectin, arabinogalactan, marmelo, locust bean gum, guar gum, tamarind seed polysaccharide, alginic acid, carrageenan, furcellaran, xanthan gum, cardran, casein, pullulan, polyvinylpyrrolidone, and polyvinyl alcohol. These may be used alone, or in mixture of two or more thereof.

The amount of such a dispersant to be added is generally 3% by weight or less based on the amount of the suspension. It is particularly desirable to be 1% by weight or less in order not to impair the rapid dissolvability of the preparation of the present invention, and conduct lyophilization in a short period of time.

For the rapidly dissolving solid preparation in the third embodiment of the present invention, the size and shape as the preparation form are not particularly limited. For example, it can be formed in a granule, pellet, tablet, suppository, or the like, as the ordinary preparation form, and a tablet form is especially preferable.

Such a rapidly dissolving solid preparation can be specifically manufactured by the following method. That is, a drug is dissolved and/or dispersed in an aqueous solution of a saccharide, if required, together with a dispersant, and further other additives such as perfumes and sweetening agents described below to form a suspension composition. Subsequently, the composition is charged into a hole of a desired preparation mold, for example, a concave mold, and lyophilized to obtain an objective solid preparation.

The rapidly dissolving solid preparation in the third embodiment of the present invention produced by aforementioned method has a practical hardness, very rapid disintegration and solubility in the oral cavity and the like even being ingested without water.

As the foregoing drugs to be used in the rapidly dissolving solid preparation in the first to third embodiment of the present invention, the type thereof is not particularly limited, and various drugs can be added thereto.

Typical examples of the drugs include: drugs for central nerves such as sedative hypnotic, antiepileptic, antipyretic analgesic antiphlogistic, analeptic, psychostimulant, diziness suppressing drug, and drug for psychoneurosis; drugs for peripheral nerves such as skeletal muscle relaxant, autonomic drugs, autonomic blocking agent, and plant preparation; drugs for sensitive organs such as drugs for ophthalmology and drugs for otolaryngology; and drugs for circulatory organs such as cardiac stimulant, antiarrhythmic agent, diuretics, antihypertensive agent, capillary stabilizers, vasoconstrictor, vasodilator, and drugs for arteriosclerosis.

There can be further mentioned drugs for respiratory tract such as respiratory stimulant and antitussive expectorant; drugs for digestive organs such as drugs for peptic ulcer, stomachic digestant, antacid, cathartic, choleretic drugs, and drugs for intestinal disorders; hormone drugs such as hormone drugs and antihormone drugs; drugs for urogenital organs and anus such as urinary antiseptics, uterotonic, drugs for urogenital organs, drugs for hemorrhoid, and drugs for anus; metabolic drugs such as vitamins, nutrient sthenia alteratives, drugs for blood and humor, drugs for hepatic disease, antidote, drugs for habitual intoxication, arthrifuge, enzyme preparations, and antidiabetic agents; drugs for functions of tissue cells such as drugs for cell activation and drugs for tumors; drugs against pathogenic organisms such as antibiotic, chemotherapeutics, antiprotozoals, and anthelmintic; and narcotics such as alkaloid type narcotics and non-alkaloid type narcotics. These drugs may be used alone, or in combination of two or more thereof.

These drugs may be in the solid, powder, or liquid form. If the solid drug is subjected to fine grinding, and used in the form of fine powder, it has a smooth feeling when it disintegrates and dissolves in the oral cavity, and hence it provides a good feeling for ingestion. Further, the drugs to be used in the present invention may also be the capsulated ones such as a microcapsule, a microsphere, a nanocapsule, and a nanosphere, and two or more drugs can also be combined in different layers.

In the foregoing rapidly dissolving solid preparation in the first to the third embodiment of the present invention, it is possible to further add natural or synthetic polymer compounds which serve as dispersants, as other formulation ingredients, within such a range as not to considerably deteriorate the disintegration, solubility, and hardness. Further, if desired, it is possible to add any one or more of sweetening agents, sour agents, perfumes, and coloring agents.

Specific examples of such natural or synthetic polymer compounds include starches and derivatives thereof such as potato starch, corn starch, rice starch, wheat starch, α-starch, partly pregelatinized starch, carboxymethyl starch sodium, and hydroxypropyl starch; and celluloses and derivatives thereof such as crystalline cellulose, methyl cellulose, hydroxypropylmethyl cellulose, hydroxypropyl cellulose, low-substituted degree hydroxypropyl cellulose, ethyl cellulose, carboxymethyl cellulose, carboxymethyl cellulose calcium, carboxymethyl cellulose sodium, sodium low substituted degree carboxymethyl cellulose, croscarmellose sodium, cellulose acetate, cellulose acetate phthalate, hydroxypropylmethyl cellulose phthalate, hydroxypropylmethyl cellulose acetate succinate, carboxymethylethyl cellulose, and crystalline cellulose - carboxymethyl cellulose sodium.

There can be further mentioned natural polymer compounds such as powdered acacia, tragant gum, karaya gum, gaty gum, pectin, arabinogalactan, marmelo, locust bean gum, guar gum, tamarind seed polysaccharide, alginic acid, carrageenan, furcellaran, xanthan gum, cardran, casein, pullulan, and albumin; and synthetic polymer compounds such as polyvinylpyrrolidone, polyvinyl acetate, macrogol, polyvinyl alcohol, aminoalkyl methacrylate copolymer E, aminoalkyl methacrylate copolymer RS, methacrylic acid copolymer L, methacrylic acid copolymer LD, methacrylic acid copolymer S, carboxyvinyl polymer, polyvinylacetal diethylaminoacetate, and dimethyl polysiloxane.

Specific examples of the sweetening agents include glycyrrhizine, disodium glycyrrhizinate, trisodium glycyrrhizinate, stevia, stevioside, levaudioside, saccharin, sodium saccharin, and aspartame.

Further, specific examples of the sour agents include citric acid, tartaric acid, and malic acid. Specific examples of the perfumes include strawberry, lemon, lemon lime, orange, peppermint, mint oil, and menthol. Specific example of the coloring agents include caramel, annatto extracted pigment, β-carotene and beet red.

EXAMPLES

The rapidly dissolving solid preparation in the first to the third embodiment of the present invention will be described in more details by way of the following examples, which should not be construed as limiting the scope of the present invention.

A: Rapidly Dissolving Solid Preparation in the First Embodiment

Example 1

First, 37.5 g of quazepam, 415 g of mannitol, 5 g of aspartame, and 2.5 g of 1-menthol were homogeneously mixed. Then, to the mixed powder was added and mixed a solution of 40 g of sucrose dissolved in 200 g of purified water to obtain a creamy suspension. The resulting suspension was charged in an amount of 280 mg into concave hole with a diameter of 9 mm, and air-dried at 30° C. for 24 hours, resulting in a rapidly dissolving preparation of the present invention.

Example 2

37.5 g of quazepam, 415 g of mannitol, 5 g of aspartame, 2.5 g of 1-menthol, and 40 g of sucrose were homogeneously mixed. Then, to the mixed powder was added and mixed 200 g of purified water to obtain a creamy suspension. The resulting suspension was charged in an amount of 280 mg into concave hole with a diameter of 9 mm, and air-dried at 30° C. for 24 hours, resulting in a rapidly dissolving preparation of the present invention.

Example 3

50 g of meclizine hydrochloride, 2 g of chlorpheniramine maleate, 20 g of pyridoxine hydrochloride, 452 g of mannitol, 400 g of lactose, 24 g of aspartame, and 12 g of 1-menthol were homogeneously mixed and put into a solution of 80 g of sucrose dissolved in 420 g of purified water, and mixed to obtain a creamy suspension. The resulting suspension was charged in an amount of 365 mg into concave hole with a diameter of 11 mm, and air-dried at 30° C. for 36 hours, resulting in a rapidly dissolving preparation of the present invention.

Example 4

First, 1 g of Epimedium grandiflorum dried extract, 2 g of Corni Fructus extract, 7.5 g of Cervi Parvum Cornu extract, 1.5 g of PolygoniMultiflori Radix dried extract, 4.5 g of Ginseng Radix dried extract, 1 g of Rehmanniae Radix dried extract, 5 g of Ophiopogonis Tuber dried extract, 0.5 g of bisbentiamine, 0.5 g of pyridoxine hydrochloride, 3 mg of cyanocobalamin, 2.5 g of caffeine, 10 g of crystalline cellulose, 120 g of mannitol, 2 g of trehalose, and 1.6 g of sucrose were mixed. To the resulting mixed powder was added 60 g of purified water to obtain a creamy suspension. The resulting suspension was charged in an amount of 219.6 mg into every concave hole with a diameter of 20 mm, and air-dried at 30° C. for 12 hours, followed by suction drying for 12 hours. Thus, a rapidly dissolving preparation of the present invention was obtained.

Example 5

25 g of pirenzepine hydrochloride, 160 g of mannitol, 20 g of lactose, 20 g of sucrose, 20 g of corn starch, 2 g of aspartame, and 1 g of 1-menthol were homogeneously mixed, and 100 g of purified water was poured thereto and mixed to obtain a creamy suspension. The resulting suspension was charged in an amount of 348 mg into concave hole with a diameter of 11 mm, and air-dried at 30° C. for 12 hours followed by suction drying for 12 hours, resulting in a rapidly dissolving preparation of the present invention.

Test Example 1

The hardness of each of the preparations manufactured in the foregoing Examples 1 to 5 was measured with a tablet hardness tester (TH-303RP type) manufactured by Toyama Sangyo. The disintegration time was also measured in accordance with the amended disintegration test listed in Japanese Pharmacopoeia 13 using purified water as a test liquid. Further, the dissolution time in the oral cavity was measured.

These results are summarized in Table 1.

TABLE 1

| | Hardness, disintegration time and dissolution time in the oral cavity | | |
| --- | --- | --- | --- |
| Example | Hardness (Kg) (Mean value of 10 samples) | Disintegration time (second) (Mean value of 6 samples) | Dissolution time in the oral cavity (second) (Mean value of 3 persons) |
| Example 1 | 6.62 | 66.0 | 53.3 |
| Example 2 | 4.83 | 51.8 | 46.7 |
| Example 3 | 3.54 | 37.3 | 38.0 |
| Example 4 | 6.37 | 79.8 | 58.3 |
| Example 5 | 8.73 | 23.2 | 47.3 |

As apparent from the results in the table, it can be understood that, the solid preparation of the present invention is particularly excellent in having a practical hardness, and a dissolution time in the oral cavity of about 1 minute or less.

Example 6

25 g of dichlofenac sodium, 170 g of mannitol, 12 g of citric acid, 20 g of corn starch, 2 g of aspartame, and 1 g of perfume were homogeneously mixed, and a solution of 20 g of sucrose dissolved in 100 g of purified water was poured thereto and mixed to obtain a creamy suspension. The resulting suspension was charged in an amount of 350 mg into concave hole with a diameter of 10 mm, and air-dried at 30° C. for 8 hours, followed by suction drying for 10 hours, resulting in a rapidly dissolving preparation of the present invention.

Example 7

20 g of piroxicam, 175 g of mannitol, 12 g of citric acid, 20 g of corn starch, 2 g of aspartame, and 1 g of perfume were homogeneously mixed, and a solution of 20 g of sucrose dissolved in 100 g of purified water was poured thereto and mixed to obtain a creamy suspension. The resulting suspension was charged in an amount of 350 mg into concave hole with a diameter of 10 mm, and air-dried at 30° C. for 8 hours, followed by suction drying for 10 hours, resulting in a rapidly dissolving preparation of the present invention.

Example 8

25 g of bisbentiamine, 196 g of mannitol, 2 g of aspartame, and 2 g of perfume were homogeneously mixed, and a solution of 20 g of sucrose dissolved in 120 g of purified water was poured thereto and mixed to obtain a creamy suspension. The resulting suspension was charged in an amount of 365 mg into concave hole with a diameter of 10 mm, and air-dried at 30° C. for 8 hours, followed by suction drying for 10 hours, resulting in a rapidly dissolving preparation of the present invention.

Test Example 2

The dissolution time in the oral cavity of each of the preparations manufactured in Examples 6 to 8 was determined.

The results are shown in Table 2.

TABLE 2

Dissolution time in the oral cavity

| Example | Dissolution time in the oral cavity (second) (Mean value of 3 persons) |
|---|---|
| Example 6 | 36.3 |
| Example 7 | 26.7 |
| Example 8 | 18.7 |

As apparent from the results in the table, it can be understood that, the preparation of the present invention is particularly excellent in having a dissolution time in the oral cavity of about 30 seconds or less.

B: Rapidly Dissolving Solid Preparation in the Second Embodiment

Example 9

15 g of quazepam, 169.5 g of sucrose, 50 g of corn starch, 2 g of aspartame, and 0.5 g of 1-menthol were homogeneously mixed. Next, the mixed powder was added and mixed with a solution of 12.5 g of polyvinylpyrrolidone dissolved in 150 g of ethanol to obtain a suspension. The resulting suspension was charged in an amount of 400 mg into concave hole with a diameter of 9 mm, and air-dried at 30° C. for 3 hours, followed by suction drying for 12 hours, resulting in a rapidly dissolving preparation of the present invention.

Examples 10 to 19

In Examples 10 to 19, the rapidly dissolving preparations of the present invention were obtained in the same manner, except that the saccharides described below were used in place of the sucrose used in Example 9.

Example 10 . . . Trehalose
Example 11 . . . Mannitol
Example 12 . . . Erythritol
Example 13 . . . Sorbitol
Example 14 . . . Lactose
Example 15 . . . Powder reduced maltose starch syrup
Example 16 . . . Xylitol
Example 17 . . . Glucose
Example 18 . . . Fructose
Example 19 . . . Dextrin

Test Example 3

The hardness of each of the preparations manufactured in Examples 9 to 19 was measured by the same method as in Test Example 1. Further, the disintegration time and the dissolution time in the oral cavity thereof were measured.

The results are summarized in Table 3.

TABLE 3

Hardness, disintegration time and dissolution time in the oral cavity

| Example | Hardness (Kg) (Mean value of 10 samples) | Disintegration time (second) (Mean value of 6 samples) | Dissolution time in the oral cavity (second) (Mean value of 3 persons) |
|---|---|---|---|
| Example 9 | 1.56 | 8.0 | 37.7 |
| Example 10 | 1.80 | 6.3 | 37.3 |
| Example 11 | 2.12 | 6.3 | 18.3 |
| Example 12 | 2.53 | 6.5 | 15.3 |
| Example 13 | 2.01 | 9.5 | 31.0 |
| Example 14 | 1.95 | 7.2 | 16.3 |
| Example 15 | 1.43 | 12.5 | 26.3 |
| Example 16 | 2.88 | 6.5 | 13.3 |
| Example 17 | 1.92 | 10.3 | 17.0 |
| Example 18 | 3.59 | 16.3 | 31.0 |
| Example 19 | 2.22 | 15.3 | 41.3 |

As apparent from the results in the table, it can be understood that, the preparations of the present invention is particularly excellent in having a practical hardness and a dissolution time in the oral cavity of about 30 seconds or less.

Example 20

15 g of quazepam, 177 g of sucrose, 50 g of corn starch, 2 g of aspartame, 0.5 g of 1-menthol, and 5 g of polyvinylpyrrolidone were homogeneously mixed. Next, the mixed powder was added and mixed with 150 g of ethanol to obtain a suspension. The resulting suspension was charged in an amount of 400 mg into concave hole with a diameter of 9 mm, and air-dried at 30° C. for 3 hours, followed by suction drying for 12 hours, resulting in a rapidly dissolving preparation of the present invention.

Example 21

The rapidly dissolving preparation of the present invention was obtained In the same manner, except that the amount of sucrose and the amount of polyvinylpyrrolidone in Example 20 were changed into 157 g and 25 g, respectively.

Example 22

The rapidly dissolving preparation of the present invention was obtained in the same manner, except that the amount of sucrose and the amount of polyvinylpyrrolidone In Example 20 were changed into 144.5 g and 37.5 g, respectively.

Comparative Example 1

A preparation of Comparative Example 1 was obtained in the same manner, except that the amount of sucrose and the amount of polyvinylpyrrolidone in Example 20 were changed Into 127 g and 55 g, respectively.

Comparative Example 2

A preparation of Comparative Example 2 was obtained in the same manner, except that the amount of sucrose in Example 20 was changed into 182 g and polyvinylpyrrolidone was not used.

Test Example 4

The hardness and the disintegration time of each of the preparations manufactured in Examples 20 to 22, and each preparation of Comparative Examples 1 and 2 described above were measured by the same method as in Test Example 1.

The results are summarized in Table 4.

TABLE 4

| | Hardness and Disintegration Time | | |
|---|---|---|---|
| Example | Amount of polyvinyl-pyrrolidone to be added | Hardness (Kg) (Mean value of 10 samples) | Disintegration time (second) (Mean value of 6 samples) |
| Example 20 | 2 | 1.03 | 6.0 |
| Example 21 | 10 | 2.80 | 55.0 |
| Example 22 | 15 | 5.83 | 58.0 |
| Comparative Example 1 | 22 | 8.24 | 271.8 |
| Comparative Example 2 | 0 | 0.30 | 1.2 |

As apparent from the results in the table, the preparation of Comparative Example 2 to which polyvinylpyrrolidone has not been added was very brittle. Further, for the preparation of Comparative Example 1 to which polyvinylpyrrolidone has been added in a large amount, the disintegration time was as long as 4 minutes or more. In contrast to this, it can be understood that the preparation of the present invention is particularly excellent in exhibiting a practically acceptable hardness and a high disintegration rate.

Example 23

15 g of quazepam, 179.5 g of sucrose, 50 g of corn starch, 2 g of aspartame, 0.5 g of l-menthol, and 2.5 g of polyvinylpyrrolidone were homogeneously mixed. Next, the mixed powder was added and mixed with a mixed solution of 105 g of ethanol and 45 g of water to obtain a suspension. The resulting suspension was charged in an amount of 400 mg into concave hole with a diameter of 9 mm, and air-dried at 30° C. for 3 hours, followed by suction drying for 12 hours, resulting in a rapidly dissolving preparation of the present invention.

The hardness of this preparation was 1.58 Kg (mean value of 10 samples), the disintegration time thereof was 8.3 sec. (mean value of 6 samples), and the dissolution time in the oral cavity was 37.3 sec. (mean value of 3 persons).

Example 24

30 g of pyridoxal hydrochloride, 151 g of erythritol, 50 g of corn starch, 1 g of citric acid, 1 g of aspartame, and 2 g of perfume were homogeneously mixed. Next, the mixed powder was added and mixed with a solution of 15 g of polyvinylpyrrolidone dissolved in 110 g of ethanol to obtain a suspension. The resulting suspension was charged in an amount of 360 mg into concave hole with a diameter of 10 mm, and air-dried at 30° C. for 3 hours, followed by suction drying for 12 hours, resulting in a rapidly dissolving preparation of the present invention.

The dissolution time of this preparation in the oral cavity was 19.7 sec. (mean value of 3 persons).

Example 25

30 g of pyridoxal hydrochloride, 151 g of xylitol, 50 g of corn starch, 1 g of citric acid, 1 g of aspartame, and 2 g of perfume were homogeneously mixed. Next, the mixed powder was added and mixed with a solution of 15 g of polyvinylpyrrolidone dissolved in 100 g of ethanol to obtain a suspension. The resulting suspension was charged in an amount of 350 mg into concave hole with a diameter of 10 mm, and air-dried at 30° C. for 3 hours, followed by suction drying for 15 hours, resulting in a rapidly dissolving preparation of the present invention.

The dissolution time of this preparation in the oral cavity was 16 sec. (mean value of 3 persons).

C: Rapidly Dissolving Solid Preparation in the Third Embodiment

Example 26

50 g of trehalose was dissolved in 200 g of purified water, and to this solution 15 g of quazepam, 5 g of perfume, 4.5 g of aspartame, and 0.5 g of xanthan gum were added and homogeneously mixed to obtain a suspension. The resulting suspension was charged in an amount of 275 mg into concave hole with a diameter of 9 mm, and lyophilized, resulting in a rapidly dissolving preparation of the present invention.

Example 27

50 g of trehalose was dissolved in 200 g of purified water, and to this solution 20 g of piroxicam, 2 g of perfume, 5 g of aspartame, and 1 g of guar gum were added and homogeneously mixed to obtain a suspension. The resulting suspension was charged in an amount of 278 mg into concave hole with a diameter of 9 mm, and lyophilized, resulting in a rapidly dissolving preparation of the present invention.

Example 28

50 g of dextrin was dissolved in 200 g of purified water, and to this solution 15 g of quazepam, 5 g of perfume, 4.5 g of aspartame, and 0.5 g of guar gum were added and homogeneously mixed to obtain a suspension. The resulting suspension was charged in an amount of 275 mg into concave hole with a diameter of 9 mm, and lyophilized, resulting in a rapidly dissolving preparation of the present invention.

Example 29

73 g of dextrin was dissolved in 292 g of purified water, and to this solution 25 g of dichlofenac sodium, 10 g of citric acid, 3 g of perfume, 6 g of aspartame, and 1 g of guar gum were added and homogeneously mixed to obtain a suspension. The resulting suspension was charged in an amount of 410 mg into concave hole with a diameter of 10 mm, and lyophilized, resulting in a rapidly dissolving preparation of the present invention.

Test Example 5

The hardness of each of the preparations manufactured in Examples 26 to 29 was measured by the same method as in Test Example 1. Further, the disintegration time and the dissolution time in the oral cavity thereof were measured.

The results are summarized in Table 5.

TABLE 5

Hardness, disintegration time and dissolution time in the oral cavity

| Example | Hardness (Kg) (Mean value of 10 samples) | Disintegration time (second) (Mean value of 6 samples) | Dissolution time in the oral cavity (second) (Mean value of 3 persons) |
| --- | --- | --- | --- |
| Example 26 | 1.23 | 10.17 | 6.0 |
| Example 27 | 1.12 | 7.33 | 5.3 |
| Example 28 | 1.43 | 6.17 | 4.3 |
| Example 29 | 1.50 | 4.83 | 5.3 |

As apparent from the results in the table, it can be understood that the preparations of the present invention is particularly excellent in having a practical hardness, a disintegration time of 10 seconds or less, and further a dissolution time in the oral cavity of about 6 seconds or less, indicating a rapid solubility.

INDUSTRIAL APPLICABILITY

As described above, since the rapidly dissolving solid preparation provided by the present invention rapidly dissolves in the oral cavity, it is easy for patients having a difficulty in swallowing such as elderly persons and children, to ingest, and it can be ingested even without water. Therefore, it can be ingested anywhere whenever the drug is required, and the compliance can be improved. Further, it has a practical hardness as well as a low hygroscopicity. Accordingly, it is easy to handle for ingestion, the storage is also easy, and thus the ordinary handling thereof is simple. Thus, the utility from the medical viewpoint is enormous.

What is claimed is:

1. A method of producing an uncompressed rapidly dissolving solid preparation comprising:

mixing a drug with a saccharide having a solubility of 30 g or less in 100 g of water at room temperature, and a saccharide having a solubility of 30 g or more in 100 g of water at room temperature, in water in such an amount as not to completely dissolve said saccharide having a solubility of 30 g or less in 100 g of water at room temperature, to form a mixture;

charging the mixture in a mold without the application of pressure; and removing the moisture therefrom.

2. The method according to claim 1, wherein said saccharide having a solubility of 30 g or less in 100 g of water at room temperature is at least one of lactose and mannitol.

3. The method according to claim 1, wherein said saccharide having a solubility of 30 g or more in 100 g of water at room temperature is at least one of glucose, fructose, sucrose, xylose, trehalose, xylitol, sorbitol, erythritol, dextrin, and pullulan.

4. A method of producing a rapidly dissolving solid preparation, comprising the steps of:

mixing a drug, a saccharide having a solubility of 30 g or less in 100 g of water at room temperature, and a saccharide having a solubility of 30 g or more in 100 g of water at room temperature, in water in such an amount as not to completely dissolve said saccharide having a solubility of 30 g or less in 100 g of water at room temperature; and removing the moisture therefrom, wherein the content of said drug is 60% by weight or less based on a total solid content, and the content of said saccharide having a solubility of 30 g or less in 100 g of water at room temperature and said saccharide having a solubility of 30 g or more in 100 g of water at room temperature is 40% by weight or more based on a total solid content in said preparation.

5. A method of producing a rapidly dissolving solid preparation, comprising the steps of:

mixing a drug, a saccharide having a solubility of 30 g or less in 100 g of water at room temperature, and a saccharide having a solubility of 30 g or more in 100 g of water at room temperature, in water in such an amount as not to completely dissolve said saccharide having a solubility of 30 g or less in 100 g of water at room temperature; and removing the moisture therefrom, wherein the content of said drug is 40% by weight or less based on a total solid content, and the content of said saccharide having a solubility of 30 g or less in 100 g of water at room temperature and said saccharide having a solubility of 30 g or more in 100 g of water at room temperature is 60% by weight or more based on a total solid content in said preparation.

6. The method according to claim 1, wherein the mixing ratio of said saccharide having a solubility of 30 g or less in 100 g of water at room temperature to said saccharide having a solubility of 30 g or more in 100 g of water at room temperature is in a range of 98:2 to 80:20 on a solid content weight basis.

7. A method of producing an uncompressed rapidly dissolving solid preparation, comprising:

dissolving and dispersing a drug, a saccharide, and polyvinylpyrrolidone in an organic solvent, to form a mixture;

charging the resultant mixture in a mold without the application of pressure; and removing the organic solvent therefrom.

8. The method according to claim 7, wherein said drug is in an amount of 60% by weight or less based on a total solid content, said saccharide is in an amount of 40% by weight or more based on a total solid content, and polyvinylpyrrolidone is in an amount of 1 to 20% by weight based on a total solid content.

9. The method according to claim 7, wherein said drug is in an amount of 40% by weight or less based on a total solid content, said saccharide is in an amount of 60% by weight or more based on a total solid content, and polyvinylpyrrolidone is in an amount of 2 to 15% by weight based on a total solid content.

10. The method according to claim 7, wherein said organic solvent is ethanol, or a mixed solution of ethanol and water.

11. A method of producing an uncompressed rapidly dissolving solid preparation, comprising:

dissolving and/or dispersing a drug in an aqueous solution of at least one saccharide selected from the group consisting of lactose, trehalose, mannitol, sorbitol, erythritol and dextrin, in which a concentration of said aqueous solution of the saccharide is in a range of 10 to 30% by weight;

charging the resultant mixture in a mold without the application of pressure to form a mixture; and lyophilizing said mixture.

12. The method according to claim 11, wherein said saccharide is at least one of trehalose and dextrin.

13. The method according to claim 11, wherein the concentration of said aqueous solution of the saccharide is in a range of 15 to 25% by weight.

14. The method according to claim 1, wherein a natural or synthetic polymer is further added.

15. The method according to claim 1, wherein at least one of a sweetening agent, sour agent, perfume, and coloring agent is further added.

16. The method according to claim 7, wherein a natural or synthetic polymer is further added.

17. The method according to claim 11, wherein a natural or synthetic polymer is further added.

18. The method according to claim 17, wherein said natural or synthetic polymer to be added is at least one selected from the group consisting of: α-starch, partly pregelatinized starch, carboxymethyl starch sodium, methyl cellulose, hydroxypropylmethyl cellulose, hydroxypropyl cellulose, carboxymethylcellulose sodium, powdered acacia, tragant gum, karaya gum, gaty gum, pectin, arabinogalactan, marmelo, locust bean gum, guar gum, tamarind seed polysaccharide, alginic acid, carrageenan, furcellaran, xanthan gum, cardran, casein, pullulan, polyvinylpyrrolidone, and polyvinyl alcohol.

19. The method according to claim 7, wherein at least one of a sweetening agent, sour agent, perfume, and coloring agent is further added.

20. The method according to claim 11, wherein at least one of a sweetening agent, sour agent, perfume, and coloring agent is further added.

* * * * *